United States Patent
During

(10) Patent No.: US 10,265,300 B2
(45) Date of Patent: Apr. 23, 2019

(54) METHODS OF TREATING SEIZURE DISORDERS

(71) Applicant: Ovid Therapeutics Inc., New York, NY (US)

(72) Inventor: Matthew During, Weston, CT (US)

(73) Assignee: OVID THERAPEUTICS INC., New York, NY (US)

( * ) Notice: Subject to any disclaimer, the term of this patent is extended or adjusted under 35 U.S.C. 154(b) by 0 days.

(21) Appl. No.: 15/904,901

(22) Filed: Feb. 26, 2018

(65) Prior Publication Data

US 2018/0243266 A1 Aug. 30, 2018

Related U.S. Application Data

(60) Provisional application No. 62/463,191, filed on Feb. 24, 2017.

(51) Int. Cl.
*A61P 25/08* (2006.01)
*A61K 31/404* (2006.01)

(52) U.S. Cl.
CPC ............ *A61K 31/404* (2013.01); *A61P 25/08* (2018.01)

(58) Field of Classification Search
CPC .............................. A61K 31/405; A61P 25/08
USPC ......................................... 514/419, 411, 418
See application file for complete search history.

(56) References Cited

U.S. PATENT DOCUMENTS

| | | |
|---|---|---|
| 5,565,483 A | 10/1996 | Hewawasam et al. |
| 2002/0045566 A1 | 4/2002 | Gribkoff et al. |
| 2014/0221450 A1 | 8/2014 | Briault et al. |
| 2017/0014392 A1 | 1/2017 | During |

FOREIGN PATENT DOCUMENTS

WO   WO-0230868 A1 * 4/2002 ............. A61K 31/40

OTHER PUBLICATIONS

Jensen, "BMS-204352: A Potassium Channel Opener Developed for the Treatment of Stroke," CNS Drug Reviews, vol. 8, No. 4, (2002); pp. 353-360.
Zhang et al., "Metabolism, Pharmacokinetics, and Protein Covalent Binding of Radiolabeled Maxipost (BMS-204352) in Humans," Drug Metabolism and Disposition, vol. 33, No. 1, (2005); pp. 83-93.
Tolman et al., "Treatment options for refractory and difficult to treat seizures: focus on vigabatrin," Therapeutics and Clinical Risk Management, 2011, vol. 7; pp. 367-375.
Krishna et al., "Disposition of Radiolabeled BMS-204352 in Rats and Dogs," Biopharmaceutics & Drug Disposition, vol. 23, (2002); pp. 41-46.
Krishna et al., "Effect of Dose and Input Rate on the Brain Penetration of BMS-204352 Following Intravenous Administration to Rats," Biopharmaceutics & Drug Disposition, vol. 23, (2002); pp. 227-231.
Krishna et al., "Pharmacokinetics and Dose Proportionality of BMS-204352 After Intraarterial Administration to Rats," Biopharmaceutics & Drug Disposition, vol. 23, (2002); pp. 233-237.
International Search Report and Written Opinion of the International Searching Authority, dated Apr. 19, 2018, corresponding to International Application No. PCT/US18/19689; 7 total pages.

* cited by examiner

*Primary Examiner* — Kevin E Weddington
(74) *Attorney, Agent, or Firm* — Carter, DeLuca & Farrell, LLP

(57) ABSTRACT

Methods of treating a seizure disorder with a maxi-K channel opener or a pharmaceutically acceptable salt thereof are provided. In embodiments, suitable maxi-K channel openers are be fluoro-oxindole or chloro-oxindole compounds. In some embodiments, the maxi-K channel opener may be (3S)-(+)-(5-chloro-2-methoxyphenyl)-1,3-dihydro-3-fluoro-6 -(trifluoromethyl)-2H-indole-2-one or pharmaceutically acceptable salts thereof. The methods provide therapeutic compositions that may be used to improve one or more symptoms of a seizure disorder.

17 Claims, No Drawings

METHODS OF TREATING SEIZURE DISORDERS

CROSS REFERENCE TO RELATED APPLICATIONS

This application claims benefit of and priority to U.S. Provisional Application No. 62/463,191, filed Feb. 24, 2017, which is incorporated herein by reference in its entirety.

TECHNICAL FIELD

Methods of treating seizure disorders are provided.

BACKGROUND

Seizure disorders typically involve abnormal nerve cell activity in the brain, causing seizures which may be manifested by periods of unusual behavior, sensations, diminished consciousness and sometimes loss of consciousness. Seizures can be a symptom of many different disorders that can affect the brain. Epilepsy is a seizure disorder characterized by recurrent seizures. See, e.g., Blume et al., Epilepsia. 2001; 42:1212-1218. Epileptic seizures are usually marked by abnormal electrical discharges in the brain and typically manifested by sudden brief episodes of altered or diminished consciousness, or involuntary movements. Non-epileptic seizures may or may not be accompanied by abnormal electrical activity in the brain and may be caused by psychological issues or stress. Drug or alcohol withdrawal can also cause seizures. Seizure symptoms can vary widely. Some seizures can hardly be noticed, while others are totally disabling. Seizure disorders include epilepsy.

Medications are used to treat seizure disorders and can be referred to as anti-epileptic drugs ("AED"). The treatment of recurrent seizures predominantly centers on the utilization of at least one AED, with possible adjunctive use of a second or even third agent in the case of monotherapeutic failure. See, Tolman and Faulkner, Ther Clin Risk Manag. 2011; 7: 367-375. However, approximately 30%-40% of epileptic patients have inadequate seizure control with just one AED, and require the use of adjunctive agents. Id. A subset of this group will have regular and persistent seizure activity despite reasonable doses of multiple AEDs. These seizures are considered refractory to treatment. Id. Accordingly, there remains a need for improved and/or additional therapies for treating seizure disorders.

SUMMARY

Methods of treating a seizure disorder are provided and, in embodiments, include administering to a subject in need thereof an effective amount a maxi-K channel opener. In embodiments, methods of treating a seizure disorder include administering a maxi-K channel opener to a subject in need thereof to provide improvement in one or more symptoms of the disorder. In embodiments, methods of treating a seizure disorder include administering a maxi-K channel opener to a subject in need thereof to provide improvement in next day functioning of the subject.

In embodiments, methods of treating a seizure disorder in accordance with the present disclosure include administering to a subject in need thereof an effective amount of a maxi-K channel opener such as fluoro-oxindole and/or chloro-oxindole compounds. Suitable fluoro-oxindoles which may be administered include (3S)-(+)-(5-chloro-2-methoxyphenyl)-1,3-dihydro-3-fluoro-6-(trifluoromethyl)-2H-indole-2-one or a pharmaceutically acceptable salt thereof, (3R)-(−)-(5-chloro-2-methoxyphenyl)-1,3-dihydro-3-fluoro-6-(trifluoromethyl)-2H-indole-2-one or a pharmaceutically acceptable salt thereof, and combinations thereof. Suitable chloro-oxindoles which may be utilized include (3S)-(+)-(5-chloro-2-methoxyphenyl)-1,3-dihydro-3-chloro-6-(trifluoromethyl)-2H-indol-2-one or a pharmaceutically acceptable salt thereof, (3R)-(−)-(5-chloro-2-methoxyphenyl)-1,3-dihydro-3-chloro-6-(trifluoromethyl)-2H-indol-2-one or a pharmaceutically acceptable salt thereof, and combinations thereof.

In embodiments, the maxi-K channel opener is administered to the subject from one to four times a day. Administration may be by any appropriate route, including oral, buccal, sublingual, rectal, topical, intranasal, vaginal, parenteral, combinations thereof, and the like.

In embodiments, the seizure disorders treated in accordance with the present disclosure include epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, drug withdrawal induced seizures, alcohol withdrawal induced seizures, increased seizure activity or breakthrough seizures (increased seizure activity; also called serial or cluster seizures). In embodiments, the seizure disorder is status epilepticus.

DETAILED DESCRIPTION

Described herein are methods and compositions for treating a seizure disorder which include administering to a subject in need thereof an effective amount of a maxi-potassium (maxi-K) channel opener. The maxi-K channel, also known as BK (Big Potassium) channel, slo1, BKCa (Big Potassium Calcium) channel or KCNMA1, includes ion channels activated by calcium that are characterized by their large conductance of potassium ions ($K^+$) through cell membranes. In ordinary conditions, opening maxi-K channels results in an efflux of $K^+$ from the cell, which leads to cell membrane hyper-polarization (a decrease in the electrical potential across the cell membrane) and a decrease in cell excitability (a decrease in the probability that the cell will transmit an action potential).

In embodiments, methods of treating a seizure disorder include administering a maxi-K channel opener to a subject in need thereof to provide improvement in one or more symptoms of the disorder. In embodiments, methods of treating a seizure disorder include administering a maxi-K channel opener to a subject in need thereof to provide improvement in next day functioning of the subject.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system.

For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of seizure disorders such as epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, drug withdrawal induced seizures, alcohol withdrawal induced seizures, increased seizure activity or breakthrough seizures (also called serial or cluster seizures), measured relative to at least one symptom of the foregoing disorders.

"Improvement in next day functioning" or "wherein there is improvement in next day functioning" refers to improvement after waking from an overnight sleep period wherein the beneficial effect of administration of maxi-K channel openers applies to at least one symptom of a syndrome or disorder herein and is discernable, either subjectively by a subject or objectively by an observer, for a period of time, e.g., 2 hours, 3 hours, 4 hours, 5 hours, 6 hours, 12 hours, 24 hours, etc. after waking.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml or g·hr/ml). The area under the curve is governed by clearance. Clearance is defined as the volume of blood or plasma that is totally cleared of its content of drug per unit time (ml/min).

"Treating", "treatment" or "treat" can refer to the following: alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treating", "treat" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating", "treat" or "treatment" also refers to inhibiting the disease or condition, e.g., arresting or reducing its development or at least one clinical or subclinical symptom thereof. "Treating", "treat" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate embodiments of the disclosure herein.

"Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount", previously referred to, can also mean a dosage sufficient to alleviate one or more symptoms of a syndrome, disorder, disease, or condition being treated, or to otherwise provide a desired pharmacological and/or physiologic effect. "Effective amount" or "therapeutically effective amount" may be used interchangeably herein.

"Co-administered with", "administered in combination with", "a combination of" or "administered along with" may be used interchangeably and mean that two or more agents are administered in the course of therapy. The agents may be administered together at the same time or separately in spaced apart intervals. The agents may be administered in a single dosage form or in separate dosage forms.

"Subject in need thereof" may include individuals that have been diagnosed with a seizure disorder such as epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, drug withdrawal induced seizures, alcohol withdrawal induced seizures, increased seizure activity or breakthrough seizures (also called serial or cluster seizures). The methods may be provided to any individual including, e.g., wherein the subject is a neonate, infant, a pediatric subject (6 months to 12 years), an adolescent subject (age 12-18 years) or an adult (over 18 years). Subjects include mammals.

"Prodrug" refers to a pharmacological substance (drug) that is administered to a subject in an inactive (or significantly less active) form. Once administered, the prodrug is metabolized in the body (in vivo) into a compound having the desired pharmacological activity.

"Analog" and "Derivative" may be used interchangeably and refer to a compound that possesses the same core as the parent compound, but may differ from the parent compound in bond order, the absence or presence of one or more atoms and/or groups of atoms, and combinations thereof. Enantiomers are examples of derivatives. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

The term "pharmaceutically acceptable salt", as used herein, refers to derivatives of the compounds defined herein, wherein the parent compound is modified by making acid or base salts thereof. Example of pharmaceutically acceptable salts include, but are not limited to, nontoxic base addition salts with inorganic bases. Suitable inorganic bases such as alkali and alkaline earth metal bases include metallic cations such as sodium, potassium, magnesium, calcium and the like. The pharmaceutically acceptable salts can be synthesized from the parent compound by conventional chemical methods.

In embodiments, maxi-K channel openers which may be used in accordance with the present disclosure include 3-phenyl substituted oxindole derivatives, including fluoro-oxindole and chloro-oxindole compounds. Examples of such maxi-K channel openers include those described in U.S. Pat. Nos. 5,565,483 and 5,602,169.

Suitable fluoro-oxindoles for use in accordance with the present disclosure include (±)-(5-chloro-2-methoxyphenyl)-1,3-dihydro-3-fluoro-6-(trifluoromethyl)-2H-indol-2-one; (3S)-(+)-(5-chloro-2-methoxyphenyl)-1,3-dihydro-3-fluoro-6-(trifluoromethyl)-2H-indole-2-one; (3R)-(−)-(5-chloro-2-methoxyphenyl)-1,3-dihydro-3-fluoro-6-(trifluoromethyl)-2H-indole-2-one; pharmaceutically acceptable salts of any of the foregoing; and combinations of any of the foregoing.

Suitable chloro-oxindoles for use in accordance with the present disclosure include ((±)-(5-chloro-2-methoxyphenyl)-1,3-dihydro-3-chloro-6-(trifluoromethyl)-2H-indol-2-one; (3S)-(+)-(5-chloro-2-methoxyphenyl)-1,3-dihydro-3-chloro-6-(trifluoromethyl)-2H-indol-2-one; (3R)-(−)-(5-chloro-2-methoxyphenyl)-1,3-dihydro-3-chloro-6-(trifluoromethyl)-2H-indol-2-one; pharmaceutically acceptable salts of any of the foregoing; and combinations of any of the foregoing.

In embodiments, methods of treating a seizure disorder include administering to a subject in need thereof an effective amount of at least one fluoro-oxindole, at least one chloro-oxindole, or combinations thereof. In embodiments, methods of treating a seizure disorder include administering at least one fluoro-oxindole, at least one chloro-oxindole, or combinations thereof to a subject in need thereof to provide improvement in one or more symptoms of the disorder. In embodiments, methods of treating a seizure disorder include administering at least one fluoro-oxindole, at least one chloro-oxindole, or combinations thereof to a subject in need thereof to provide improvement in next day functioning of the subject.

In embodiments, the maxi-K channel opener is (3S)-(+)-(5-chloro-2-methoxyphenyl)-1,3-dihydro-3-fluoro-6-(trifluoromethyl)-2H-indol-2-one and/or its R-enantiomer, (3R)-(−)-(5-chloro-2-methoxyphenyl)-1,3-dihydro-3-fluoro-6-(trifluoromethyl)-2H-indole-2-one. The structure of (3S)-(+)-(5-chloro-2-methoxyphenyl)-1,3-dihydro-3-fluoro-6-(trifluoromethyl)-2H-indol-2-one may be represented as follows:

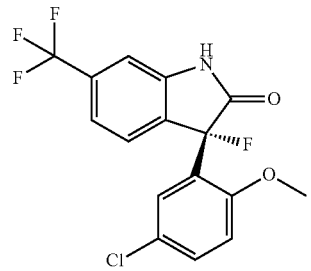 [SMILES: COc1ccc(Cl)cc1[C@]1(F)C(=O)Nc2cc(C(F)(F)F)ccc21]

The structure of the R-enantiomer of (3S)-(+)-(5-chloro-2-methoxyphenyl)-1,3-dihydro-3-fluoro-6-(trifluoromethyl)-2H-indol-2-one ((3R)-(−)-(5-chloro-2-methoxyphenyl)-1,3-dihydro-3-fluoro-6-(trifluoromethyl)-2H-indol-2-one) may be represented as follows:

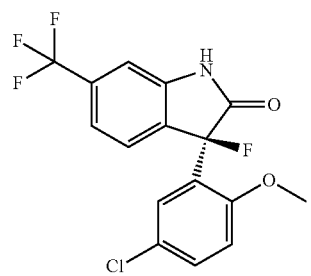 [SMILES: COc1ccc(Cl)cc1[C@@]1(F)C(=O)Nc2cc(C(F)(F)F)ccc21]

In embodiments, methods of treating a seizure disorder include administering to a subject in need thereof an effective amount of (3S)-(+)-(5-chloro-2-methoxyphenyl)-1,3-dihydro-3-fluoro-6-(trifluoromethyl)-2H-indol-2-one or a pharmaceutically acceptable salt thereof. In embodiments, methods of treating a seizure disorder include administering (3S)-(+)-(5-chloro-2-methoxyphenyl)-1,3-dihydro-3-fluoro-6-(trifluoromethyl)-2H-indol-2-one or a pharmaceutically acceptable salt thereof to a subject in need thereof to provide improvement in one or more symptoms of the disorder. In embodiments, methods of treating a seizure disorder include administering (3S)-(+)-(5-chloro-2-methoxyphenyl)-1,3-dihydro-3-fluoro-6-(trifluoromethyl)-2H-indol-2-one or a pharmaceutically acceptable salt thereof to a subject in need thereof to provide improvement in next day functioning of the subject.

Examples of seizure disorders include epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, drug withdrawal induced seizures, alcohol withdrawal induced seizures, increased seizure activity or breakthrough seizures (also called serial or cluster seizures). In embodiments, the seizure disorder is associated with a sodium channel protein type 1 subunit alpha (Scn1a)-related disorder.

In embodiments, the seizure disorder is status epilepticus (SE). SE is characterized by an epileptic seizure of greater than five minutes or more than one seizure within a five-minute period without the person returning to normal between them. SE can be a dangerous condition that can lead to mortality if treatment is delayed. SE can be convulsive, with a regular pattern of contraction and extension of the arms and legs, or non-convulsive, with a change in a person's level of consciousness of relatively long duration but without large scale bending and extension of the limbs due to seizure activity. Convulsive SE (CSE) may be further classified into (a) tonic-clonic SE, (b) tonic SE, (c) clonic SE and (d) myoclonic SE. Non-convulsive SE (NCSE) is characterized by abnormal mental status, unresponsiveness, ocular motor abnormalities, persistent electrographic seizures, and possible response to anticonvulsants.

In embodiments, provided herein are methods for treating a seizure disorder which include administering to a subject in need thereof an effective amount of a maxi-K channel opener, wherein the subject exhibits improvement in at least one symptom of the seizure disorder. In embodiments, methods of treating a seizure disorder include administering at least one fluoro-oxindole, at least one chloro-oxindole, or combinations thereof, to a subject in need thereof wherein the subject exhibits improvement in one or more symptoms of the disorder. In embodiments, methods of treating a seizure disorder include administering (3S)-(+)-(5-chloro-2-methoxyphenyl)-1,3-dihydro-3-fluoro-6-(trifluoromethyl)-2H-indol-2-one, or a pharmaceutically acceptable salt thereof, to a subject in need thereof wherein the subject exhibits improvement in one or more symptoms of the disorder.

Symptoms of a seizure disorder may include, but are not limited to, episodes involving ataxia, gait impairment, speech impairment, vocalization, impaired cognition, abnormal motor activity, clinical seizure, subclinical seizure, hypotonia, hypertonia, drooling, and mouthing behavior, aura, repetitive movements, and unusual sensations. In embodiments, the methods and compositions provided may reduce or prevent one or more different types of seizures. Generally, a seizure can include repetitive movements, unusual sensations, and combinations thereof.

Seizures can be categorized as focal seizures (also referred to as partial seizures) and generalized seizures. Focal seizures affect only one side of the brain, while generalized seizures affect both sides of the brain. Specific types of focal seizures include simple focal seizures, complex focal seizures, and secondarily generalized seizures. Simple focal seizures can be restricted or focused on a particular lobe (e.g., temporal lobe, frontal lobe, parietal lobe, or occipital lobe). Complex focal seizures generally affect a larger part of one hemisphere than simple focal seizures, but commonly originate in the temporal lobe or the frontal lobe. When a focal seizure spreads from one side (hemisphere) to both sides of the brain, the seizure is referred to as a secondarily generalized seizure. Specific types of generalized seizures include absences (also referred to as petit mal seizures), tonic seizures, atonic seizures, myoclonic seizures, tonic clonic seizures (also referred to as grand mal seizures), and clonic seizures.

In embodiments, methods include treating a seizure disorder by administering to a subject in need thereof about 0.05 mg to about 1500 mg of (3S)-(+)-(5-chloro-2-methoxyphenyl)-1,3-dihydro-3-fluoro-6-(trifluoromethyl)-2H-indole-2-one or a pharmaceutically acceptable salt thereof. In embodiments, methods include treating a seizure disorder by administering to a subject in need thereof about 0.07 mg to about 1000 mg of (3S)-(+)-(5-chloro-2-methoxyphenyl)-1,3-dihydro-3-fluoro-6-(trifluoromethyl)-2H-indole-2-one or a pharmaceutically acceptable salt thereof. In embodiments, the amount of (3S)-(+)-(5-chloro-2-methoxyphenyl)-1,3-dihydro-3-fluoro-6-(trifluoromethyl)-2H-indole-2-one or a pharmaceutically acceptable salt thereof, can be between 0.001 and 1500 mg/day, or 0.05 mg/kg/day to 500 mg/kg/day, for treatment of a seizure disorder. For example, the daily dosage can be, e.g., in the range of about 0.05 to 1500 mg, 0.05 to 1250 mg, 0.05 to 1000 mg, 0.05 to 750 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 1500 mg, 0.5 to 1250 mg, 0.5 to 1000 mg, 0.5 to 750 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for treating a seizure disorder may include (3S)-(+)-(5-chloro-2-methoxyphenyl)-1,3-dihydro-3-fluoro-6-(trifluoromethyl)-2H-indole-2-one or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Suitable dosages may be administered to a subject having a seizure disorder once, twice, three or four times daily, every other day, once weekly, or once a month. In embodiments, (3S)-(+)-(5-chloro-2-methoxyphenyl)-1,3-dihydro-3-fluoro-6-(trifluoromethyl)-2H-indole-2-one or a pharmaceutically acceptable salt thereof is administered to a subject having a seizure disorder twice a day, (e.g., morning and evening), or three times a day (e.g., at breakfast, lunch, and dinner), at a dose of 1-50 mg/administration. In embodiments, (3S)-(+)-(5-chloro-2-methoxyphenyl)-1,3-dihydro-3-fluoro-6-(trifluoromethyl)-2H-indole-2-one or a pharmaceutically acceptable salt thereof is administered to a subject having a seizure disorder 600 mg/per day, 550 mg/per day, 500 mg/per day, 450 mg/per day, 400 mg/per day, 350 mg/per day, 300 mg/per day, 250 mg/per day, 225 mg/per day, 200 mg/per day, 190 mg/per day, 180 mg/per day, 170 mg/per day, 160 mg/per day, 150 mg/per day, 140 mg/per day, 130 mg/per day, 120 mg/per day, 110 mg/per day, 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose can be about 0.05 to 500 mg per day and can be increased to 750 mg per day. Dosages can be lower for infants and children than for adults. In embodiments, an infant or pediatric dose can be about 0.1 to 50 mg per day once or in 2, 3 or 4 divided doses. In embodiments, a pediatric dose can be 0.75 mg/kg/day to 1.5 mg/kg/day. In embodiments, the subject may be started at a low dose and the dosage is escalated over time.

In embodiments, methods of treating a seizure disorder are provided which include administering to a subject in need thereof a pharmaceutical composition including (3S)-(+)-(5-chloro-2-methoxyphenyl)-1,3-dihydro-3-fluoro-6-(trifluoromethyl)-2H-indole-2-one or a pharmaceutically acceptable salt thereof wherein the composition provides improvement in one or more symptoms of the disorder for more than 1 hour after administration to the subject. In embodiments, methods of treating a seizure disorder are provided which include administering to a subject in need thereof a pharmaceutical composition including (3S)-(+)-(5-chloro-2-methoxyphenyl)-1,3-dihydro-3-fluoro-6-(trifluoromethyl)-2H-indole-2-one or a pharmaceutically acceptable salt thereof wherein the composition provides improvement in one or more symptoms of the disorder for more than 2 hours after administration to the subject. In embodiments, methods of treating a seizure disorder are provided which include administering to a subject in need thereof a pharmaceutical composition including (3S)-(+)-(5-chloro-2-methoxyphenyl)-1,3-dihydro-3-fluoro-6-(trifluoromethyl)-2H-indole-2-one or a pharmaceutically acceptable salt thereof wherein the composition provides improvement in one or more symptoms of the disorder for more than 3 hours after administration to the subject. In embodiments, methods of treating a seizure disorder are provided which include administering to a subject in need thereof a pharmaceutical composition including (3S)-(+)-(5-chloro-2-methoxyphenyl)-1,3-dihydro-3-fluoro-6-(trifluoromethyl)-2H-indole-2-one or a pharmaceutically acceptable salt thereof wherein the composition provides improvement in one or more symptoms of the disorder for more than 4 hours after administration to the subject. In embodiments, methods of treating a seizure disorder are provided which include administering to a subject in need thereof a pharmaceutical composition including (3S)-(+)-(5-chloro-2-methoxyphenyl)-1,3-dihydro-3-fluoro-6-(trifluoromethyl)-2H-indole-2-one or a pharmaceutically acceptable salt thereof wherein the composition provides improvement in one or more symptoms of the disorder for more than 6 hours after administration to the subject. In embodiments, methods of treating a seizure disorder are provided which include administering to a subject in need thereof a pharmaceutical composition including (3S)-(+)-(5-chloro-2-methoxyphenyl)-1,3-dihydro-3-fluoro-6-(trifluoromethyl)-2H-indole-2-one or a pharmaceutically acceptable salt thereof wherein the composition provides improvement in one or more symptoms of the disorder for more than 8, 10, 12, 14, 16, 18, 20, 22 or 24 hours after administration to the subject. In embodiments, improvement in at least one symptom for 12 hours after administration of the pharmaceutical composition to the subject is provided in accordance with the present disclosure. In embodiments, the pharmaceutical compositions provide improvement of next day functioning of the subject. For example, the pharmaceutical compositions may provide improvement in one or more symptoms of the disorder for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, provided herein are methods of treating a seizure disorder including administering to a subject in need thereof a pharmaceutical composition including (3S)-(+)-(5-chloro-2-methoxyphenyl)-1,3-dihydro-3-fluoro-6-(trifluoromethyl)-2H-indole-2-one or a pharmaceutically acceptable salt thereof, after a warning sign of an impending seizure is detected to reduce or prevent seizure activity.

In embodiments, the methods described herein are effective to reduce, delay, or prevent one or more other clinical symptoms of a seizure disorder. For example, the effect of a composition including (3S)-(+)-(5-chloro-2-methoxyphenyl)-1,3-dihydro-3-fluoro-6-(trifluoromethyl)-2H-indole-2-one or a pharmaceutically acceptable salt thereof, on a particular symptom, pharmacologic, or physiologic indicator can be compared to an untreated subject, or the condition of the subject prior to treatment. In embodiments, the symptom, pharmacologic, and/or physiologic indicator is measured in a subject prior to treatment, and again one or more times after treatment is initiated. In embodiments, the control is a reference level, or average determined based on measuring the symptom, pharmacologic, or physiologic indicator in one or more subjects that do not have the disease or condition to be treated (e.g., healthy subjects). In embodiments, the effect of the treatment is compared to a conventional treatment that is within the purview of those skilled in the art.

Effective treatment of a seizure disorder (e.g., acute repetitive seizure, status epilepticus) herein may be established by showing reduction in the frequency or severity of symptoms (e.g., more than 10%, 20%, 30% 40% or 50%) after a period of time compared with baseline. For example, after a baseline period of 1 month, the subjects may be randomly allocated (3S)-(+)-(5-chloro-2-methoxyphenyl)-1,3-dihydro-3-fluoro-6-(trifluoromethyl)-2H-indole-2-one or a pharmaceutically acceptable salt thereof, or placebo as add-on therapy to standard therapies, during a double-blind period of 2 months.

Primary outcome measurements may include the percentage of responders on (3S)-(+)-(5-chloro-2-methoxyphenyl)-1,3-dihydro-3-fluoro-6-(trifluoromethyl)-2H-indole-2-one or a pharmaceutically acceptable salt thereof, and on placebo, defined as having experienced at least a 10% to 50% reduction of symptoms during the second month of the double-blind period compared with baseline.

In embodiments, provided herein are methods of treating a seizure disorder including administering to a subject in need thereof (3S)-(+)-(5-chloro-2-methoxyphenyl)-1,3-dihydro-3-fluoro-6-(trifluoromethyl)-2H-indole-2-one or a pharmaceutically acceptable salt thereof, which provides an in vivo plasma profile, wherein the in vivo plasma profile of the subject 10 hours after administration of (3S)-(+)-(5-chloro-2-methoxyphenyl)-1,3-dihydro-3-fluoro-6-(trifluoromethyl)-2H-indole-2-one or a pharmaceutically acceptable salt thereof, is reduced by more than 50% and the method provides improvement in the subject for more than 10, 12, 14, 16, 18, 20, 22 or 24 hours after administration.

In embodiments, provided herein are methods of treating a seizure disorder including administering to a subject in need thereof (3S)-(+)-(5-chloro-2-methoxyphenyl)-1,3-dihydro-3-fluoro-6-(trifluoromethyl)-2H-indole-2-one or a pharmaceutically acceptable salt thereof, which provides an in vivo plasma profile, wherein the in vivo plasma profile of the subject 10 hours after administration of (3S)-(+)-(5-chloro-2-methoxyphenyl)-1,3-dihydro-3-fluoro-6-(trifluoromethyl)-2H-indole-2-one or a pharmaceutically acceptable salt thereof, is reduced by more than 55% and the method provides improvement in the subject for more than 10, 12, 14, 16, 18, 20, 22 or 24 hours after administration.

In embodiments, provided herein are methods of treating a seizure disorder including administering to a subject in need thereof (3S)-(+)-(5-chloro-2-methoxyphenyl)-1,3-dihydro-3-fluoro-6-(trifluoromethyl)-2H-indole-2-one or a pharmaceutically acceptable salt thereof, which provides an in vivo plasma profile, wherein the in vivo plasma profile of the subject 10 hours after administration of (3S)-(+)-(5-chloro-2-methoxyphenyl)-1,3-dihydro-3-fluoro-6-(trifluoromethyl)-2H-indole-2-one or a pharmaceutically acceptable salt thereof, is reduced by more than 60% and the method provides improvement in the subject for more than 10, 12, 14, 16, 18, 20, 22 or 24 hours after administration.

In embodiments, provided herein are methods of treating a seizure disorder including administering to a subject in need thereof (3S)-(+)-(5-chloro-2-methoxyphenyl)-1,3-dihydro-3-fluoro-6-(trifluoromethyl)-2H-indole-2-one or a pharmaceutically acceptable salt thereof, which provides an in vivo plasma profile, wherein the in vivo plasma profile of the subject 10 hours after administration of (3S)-(+)-(5-chloro-2-methoxyphenyl)-1,3-dihydro-3-fluoro-6-(trifluoromethyl)-2H-indole-2-one or a pharmaceutically acceptable salt thereof, is reduced by more than 65% and the method provides improvement in the subject for more than 10, 12, 14, 16, 18, 20, 22 or 24 hours after administration.

In embodiments, provided herein are methods of treating a seizure disorder wherein the amount of active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, individually or in any combination, within the subject about 4 hours after administration of the pharmaceutical composition is less than about 75% of the administered dose. In embodiments, provided herein are methods wherein the amount of (3S)-(+)-(5-chloro-2-methoxyphenyl)-1,3-dihydro-3-fluoro-6-(trifluoromethyl)-2H-indole-2-one or a pharmaceutically acceptable salt thereof, individually or in any combination, within the subject about, e.g., 6 hours, 8 hours, 10 hours, 12 hours, 15 hours, or 20 hours after administration of the pharmaceutical composition is less than about 75%.

In embodiments, provided herein are methods of treating a seizure disorder wherein the amount of active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, individually or in any combination, within the subject about 4 hours after administration of the pharmaceutical composition is less than about 80% of the administered dose. In embodiments, provided herein are methods wherein the amount of active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, individually or in any combination, within the subject about, e.g., 6 hours, 8 hours, 10 hours, 12 hours, 15 hours, or 20 hours after administration of the pharmaceutical composition is less than about 80% of the administered dose.

In embodiments, provided herein are methods of treating a seizure disorder wherein the amount of active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, individually or in any combination, within the subject about 4 hours after administration of the pharmaceutical composition is between about 65% to about 85% of the administered dose. In embodiments, the amount of active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, individually or in any combination, within the subject after about, e.g., 6 hours, 8 hours, 10 hours, 12 hours, 15 hours, or 20 hours after administration of the pharmaceutical composition is between about 65% to about 85% of the administered dose.

In embodiments, the pharmaceutical compositions described herein may be administered once daily, twice daily, three times daily, four times daily, or every other day. In embodiments, the pharmaceutical compositions described herein may be administered by continuous infusion.

In embodiments, a pharmaceutical composition described herein is provided to the subject in the morning. In embodiments, a pharmaceutical composition described herein is provided to the subject in the evening. In embodiments, a pharmaceutical composition described herein is provided to the subject once in the evening and once in the morning. In embodiments, a pharmaceutical composition described herein is provided to the subject once in the morning, once in the afternoon and once in the evening.

Suitable methods of administration include, in addition to the infusion methods described above, oral, buccal, sublingual, rectal, topical, intranasal, vaginal, parenteral, combinations thereof, and the like.

In embodiments, as mentioned previously, pharmaceutical compositions herein may be provided with conventional release or modified release profiles. Pharmaceutical compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions. Those with skill in the art are familiar with such pharmaceutical carriers and methods of compounding pharmaceutical compositions using such carriers.

In embodiments, pharmaceutical compositions herein are modified release dosage forms which provide modified release profiles. Modified release profiles may exhibit immediate release, delayed release, or extended release profiles. Conventional (or unmodified) release oral dosage forms such as tablets, capsules, suppositories, syrups, solutions and suspensions typically release medications into the mouth, stomach or intestines as the tablet, capsule shell or suppository dissolves, or, in the case of syrups, solutions and suspensions, when they are swallowed. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Subjects with seizure disorders may exhibit such behavior. ODDF's can provide rapid delivery of medication to the blood stream through mucosa resulting in a rapid onset of action. Examples of ODDFs include orally disintegrating tablets, capsules and rapidly dissolving films and wafers.

Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. Suitable formulations which provide extended release profiles are within the purview of those skilled in the art. For example, coated slow release beads or granules ("beads" and "granules" are used interchangeably herein) in which (3S)-(+)-(5-chloro-2-methoxyphenyl)-1,3-dihydro-3-fluoro-6-(trifluoromethyl)-2H-indole-2-one or a pharmaceutically acceptable salt thereof, is applied to beads, e.g., confectioners nonpareil beads, and then coated with conventional release retarding materials such as waxes, enteric coatings and the like. In embodiments, beads can be formed in which (3S)-(+)-(5-chloro-2-methoxyphenyl)-1,3-dihydro-3-fluoro-6-(trifluoromethyl)-2H-indole-2-one or a pharmaceutically acceptable salt thereof is mixed with a material to provide a mass from which the drug leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets.

In embodiments, modified dosage forms herein incorporate delayed release dosage forms having delayed release profiles. Delayed release dosage forms can include delayed release tablets or delayed release capsules. A delayed release tablet is a solid dosage form which releases a drug (or drugs) such as (3S)-(+)-(5-chloro-2-methoxyphenyl)-1,3-dihydro-3-fluoro-6-(trifluoromethyl)-2H-indole-2-one or a pharmaceutically acceptable salt thereof, at a time other than promptly after administration. A delayed release capsule is a solid dosage form in which the drug is enclosed within either a hard or soft soluble container made from a suitable form of gelatin, and which releases a drug (or drugs) at a time other than promptly after administration. For example, enteric-coated tablets, capsules, particles and beads are well-known examples of delayed release dosage forms. Enteric coated tablets, capsules and particles and beads pass through the stomach and release the drug in the intestine. In embodiments, a delayed release tablet is a solid dosage form containing a conglomerate of medicinal particles that releases a drug (or drugs) at a time other than promptly after administration. In embodiments, the conglomerate of medicinal particles are covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles are covered with a coating which delays release of the drug.

Delayed release dosage forms are within the purview of those skilled in the art. For example, coated delayed release beads or granules in which (3S)-(+)-(5-chloro-2-methoxyphenyl)-1,3-dihydro-3-fluoro-6-(trifluoromethyl)-2H-indole-2-one or a pharmaceutically acceptable salt thereof, is applied to beads, e.g., confectioners nonpareil beads, and then coated with conventional release delaying materials such as waxes, enteric coatings and the like. In embodiments, beads can be formed in which (3S)-(+)-(5-chloro-2-methoxyphenyl)-1,3-dihydro-3-fluoro-6-(trifluoromethyl)-2H-indole-2-one or a pharmaceutically acceptable salt thereof, is mixed with a material to provide a mass from which the drug leaches out. In embodiments, the beads may be engineered to provide different rates of release by varying characteristics of the coating or mass, e.g., thickness, porosity, using different materials, etc. In embodiments, enteric coated granules of (3S)-(+)-(5-chloro-2-methoxyphenyl)-1,3-dihydro-3-fluoro-6-(trifluoromethyl)-2H-indole-2-one or a pharmaceutically acceptable salt thereof, can be contained in an enterically coated capsule or tablet which releases the granules in the small intestine. In embodiments, the granules have a coating which remains intact until the coated granules reach at least the ileum and thereafter provide a delayed release of the drug in the colon. Suitable enteric coating materials are well known in the art, e.g., EUDRAGIT® coatings such methacrylic acid and methyl methacrylate polymers and others. The granules can be contained in capsules or compressed into tablets.

In embodiments, (3S)-(+)-(5-chloro-2-methoxyphenyl)-1,3-dihydro-3-fluoro-6-(trifluoromethyl)-2H-indole-2-one or a pharmaceutically acceptable salt thereof, is incorporated into porous inert carriers that provide delayed release profiles. In embodiments, the porous inert carriers incorporate channels or passages from which the drug diffuses into surrounding fluids. In embodiments, (3S)-(+)-(5-chloro-2-methoxyphenyl)-1,3-dihydro-3-fluoro-6-(trifluoromethyl)-2H-indole-2-one or a pharmaceutically acceptable salt thereof, is incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, pharmaceutical compositions described herein are suitable for parenteral administration, including, e.g., intramuscular (i.m.), intravenous (i.v.), subcutaneous (s.c.), intraperitoneal (i.p.), or intrathecal (i.t.). Parenteral compositions must be sterile for administration by injection, infusion or implantation into the body and may be packaged in either single-dose or multi-dose containers. In embodiments, liquid pharmaceutical compositions for parenteral administration to a subject include an active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, in any of the respective amounts described above. In embodiments, the pharmaceutical compositions for parenteral administration are formulated as a total volume of about, e.g., 10 ml, 20 ml, 25 ml, 50 ml, 100 ml, 200 ml, 250 ml, or 500 ml. In embodiments, the compositions are contained in a bag, a glass vial, a plastic vial, or a bottle.

In embodiments, pharmaceutical compositions for parenteral administration include respective amounts described above for (3S)-(+)-(5-chloro-2-methoxyphenyl)-1,3-dihydro-3-fluoro-6-(trifluoromethyl)-2H-indole-2-one or a pharmaceutically acceptable salt thereof. In embodiments, pharmaceutical compositions for parenteral administration include about 0.05 mg to about 500 mg active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof. In embodiments, pharmaceutical compositions for parenteral administration to a subject include an active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, at a respective concentration of about 0.005 mg/ml to about 500 mg/ml. In embodiments, the pharmaceutical composition for parenteral administration includes an active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, at a respective concentration of, e.g., about 0.05 mg/ml to about 50 mg/ml, about 0.1 mg/ml to about 50 mg/ml, about 0.1 mg/ml to about 10 mg/ml, about 0.05 mg/ml to about 25 mg/ml, about 0.05 mg/ml to about 10 mg/ml, about 0.05 mg/ml to about 5 mg/ml, or about 0.05 mg/ml to about 1 mg/ml. In embodiments, the pharmaceutical composition for parenteral administration includes an active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, at a respective concentration of, e.g., about 0.05 mg/ml to about 15 mg/ml, about 0.5 mg/ml to about 10 mg/ml, about 0.25 mg/ml to about 5 mg/ml, about 0.5 mg/ml to about 7 mg/ml, about 1 mg/ml to about 10 mg/ml, about 5 mg/ml to about 10 mg/ml, or about 5 mg/ml to about 15 mg/ml.

In embodiments, a pharmaceutical composition for parenteral administration is provided wherein the pharmaceutical composition is stable for at least six months. In embodiments, the pharmaceutical compositions for parenteral administration exhibit no more than about 5% decrease in active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, for at least, e.g., 3 months or 6 months. In embodiments, the amount of (3S)-(+)-(5-chloro-2-methoxyphenyl)-1,3-dihydro-3-fluoro-6-(trifluoromethyl)-2H-indole-2-one or a pharmaceutically acceptable salt thereof, degrades at no more than about, e.g., 2.5%, 1%, 0.5% or 0.1%. In embodiments, the degradation is less than about, e.g., 5%, 2.5%, 1%, 0.5%, 0.25%, 0.1%, for at least six months.

In embodiments, pharmaceutical compositions for parenteral administration are provided wherein the pharmaceutical composition remains soluble. In embodiments, pharmaceutical compositions for parenteral administration are provided that are stable, soluble, local site compatible and/or ready-to-use. In embodiments, the pharmaceutical compositions herein are ready-to-use for direct administration to a subject in need thereof.

The pharmaceutical compositions for parenteral administration provided herein may include one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of (3S)-(+)-(5-chloro-2-methoxyphenyl)-1,3-dihydro-3-fluoro-6-(trifluoromethyl)-2H-indole-2-one or a pharmaceutically acceptable salt thereof, used in the composition. Thus, parenteral compositions are provided wherein there is no incompatibility between any of the components of the dosage form.

In embodiments, parenteral compositions including (3S)-(+)-(5-chloro-2-methoxyphenyl)-1,3-dihydro-3-fluoro-6-(trifluoromethyl)-2H-indole-2-one or a pharmaceutically acceptable salt thereof, include a stabilizing amount of at least one excipient. For example, excipients may be selected from the group consisting of buffering agents, solubilizing agents, tonicity agents, antioxidants, chelating agents, antimicrobial agents, and preservative. One skilled in the art will appreciate that an excipient may have more than one function and be classified in one or more defined group.

In embodiments, parenteral compositions include (3S)-(+)-(5-chloro-2-methoxyphenyl)-1,3-dihydro-3-fluoro-6-(trifluoromethyl)-2H-indole-2-one, or a pharmaceutically acceptable salt thereof, and an excipient wherein the excipient is present at a weight percent (w/v) of less than about, e.g., 10%, 5%, 2.5%, 1%, or 0.5%. In embodiments, the excipient is present at a weight percent between about, e.g., 1.0% to 10%, 10% to 25%, 15% to 35%, 0.5% to 5%, 0.001% to 1%, 0.01% to 1%, 0.1% to 1%, or 0.5% to 1%. In embodiments, the excipient is present at a weight percent between about, e.g., 0.001% to 1%, 0.01% to 1%, 1.0% to 5%, 10% to 15%, or 1% to 15%.

In embodiments, parenteral compositions may be administered as needed, e.g., once, twice, thrice or four or more times daily, or continuously depending on the subject's needs.

In embodiments, parenteral compositions of an active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6.

In embodiments, provided herein are methods of treating a seizure disorder including administering to a subject in need thereof a pharmaceutical composition including an active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, in a respective amount described herein, wherein the composition provides an in vivo plasma profile having a $C_{max}$ less than about 800 ng/ml. In embodiments, the composition provides improvement for more than 6 hours after administration to the subject.

In embodiments, pharmaceutical compositions including (3S)-(+)-(5-chloro-2-methoxyphenyl)-1,3-dihydro-3-fluoro-6-(trifluoromethyl)-2H-indole-2-one or a pharmaceutically acceptable salt thereof, provide an in vivo plasma profile having a $C_{max}$ less than about, e.g., 2000 ng/ml, 1000 ng/ml, 850 ng/ml, 800 ng/ml, 750 ng/ml, 700 ng/ml, 650 ng/ml, 600 ng/ml, 550 ng/ml, 450 ng/ml, 400 ng/ml 350 ng/ml, or 300 ng/ml and wherein the composition provides improvement of next day functioning of the subject. In embodiments, the pharmaceutical composition provides an in vivo plasma profile having a $C_{max}$ less than about, e.g., 250 ng/ml, 200 ng/ml 150 ng/ml, or 100 ng/ml and wherein the composition provides improvement of next day functioning of the subject. In embodiments, the pharmaceutical composition provides improvement in one or more symptoms of a disorder herein for more than 6 hours after administration.

In embodiments, provided herein are methods of treating a seizure disorder including administering to a subject in need thereof a pharmaceutical composition containing (3S)-(+)-(5-chloro-2-methoxyphenyl)-1,3-dihydro-3-fluoro-6-(trifluoromethyl)-2H-indole-2-one or a pharmaceutically acceptable salt thereof, wherein the composition provides a consistent in vivo plasma profile having a $AUC_{0-\infty}$ of less than about 900 ng·hr/ml. In embodiments, the pharmaceutical composition provides improvement in next day functioning of the subject. In embodiments, the compositions provide an in vivo plasma profile having a $AUC_{0-\infty}$ of less than about, e.g., 850 ng·hr/ml, 800 ng·hr/ml, 750 ng·hr/ml, or 700 ng·hr/ml and wherein the pharmaceutical composition provides improvement of next day functioning of the subject. In embodiments, the composition provides improvement in one or more symptoms of a disorder herein for more than 6 hours after administration.

In embodiments, provided herein are methods of treating a seizure disorder including administering to a subject in need thereof a pharmaceutical composition comprising an active substance, e.g., (3S)-(+)-(5-chloro-2-methoxyphenyl)-1,3-dihydro-3-fluoro-6-(trifluoromethyl)-2H-indole-2-one or a pharmaceutically acceptable salt thereof, wherein the pharmaceutical composition provides an in vivo plasma profile having a $AUC_{0-\infty}$ of less than about, e.g., 650 ng·hr/ml, 600 ng·hr/ml, 550 ng·hr/ml, 500 ng·hr/ml, or 450 ng·hr/ml. In embodiments, the composition provides an in vivo plasma profile having a $AUC_{0-\infty}$ of less than about, e.g., 400 ng·hr/ml, 350 ng·hr/ml, 300 ng·hr/ml, 250 ng·hr/ml, or 200 ng·hr/ml. In embodiments, the pharmaceutical composition provides an in vivo plasma profile having a $AUC_{0-\infty}$ of less than about, e.g. 180 ng·hr/ml, 150 ng·hr/ml, 100 ng·hr/ml, 75 ng·hr/ml, or 50 ng·hr/ml. In embodiments, the pharmaceutical composition provides improvement of next day functioning of the subject after administration for more than, e.g., 4 hours, 6 hours, 8 hours, 10 hours, or 12 hours, after administration of the composition to the subject.

In embodiments, the $T_{max}$ of the pharmaceutical composition is less than 3 hours. In embodiments, the $T_{max}$ of the pharmaceutical composition is less than 2.5 hours. In embodiments, the $T_{max}$ of the pharmaceutical composition is less than 2 hours. In embodiments, the $T_{max}$ of the pharmaceutical composition is less than 1.5 hours. In embodiments, the $T_{max}$ of the pharmaceutical composition is less than 1 hour. In embodiments, the $T_{max}$ of the pharmaceutical composition is less than 0.5 hour. In embodiments, the $T_{max}$ of the pharmaceutical composition is less than 0.25 hour. In embodiments, the $T_{max}$ of the pharmaceutical composition is less than 0.2 hour. In embodiments, the $T_{max}$ of the pharmaceutical composition is less than 0.1 hour.

In embodiments, the pharmaceutical composition provides a dissolution of at least about 80% within the first 20 minutes of administration to a subject in need thereof. In embodiments, the pharmaceutical composition provides a dissolution of at least about, e.g., 85%, 90% or 95% within the first 20 minutes of administration to a subject in need thereof. In embodiments, the pharmaceutical composition provides a dissolution of at least 80% within the first 10 minutes of administration to a subject in need thereof.

In embodiments, improvement in at least one symptom of a seizure disorder for more than 8 hours after administration to the subject is provided. In embodiments, improvement for more than about, e.g., 10 hours, 12 hours, 15 hours, 18 hours, 20 hours, 24 hours, 30 hours, 36 hours, 42 hours or 48 hours after administration to the subject is provided.

In embodiments, the pharmaceutical composition is provided to the subject once in the evening and once in the morning. In embodiments, the total amount of (3S)-(+)-(5-chloro-2-methoxyphenyl)-1,3-dihydro-3-fluoro-6-(trifluoromethyl)-2H-indole-2-one or a pharmaceutically acceptable salt thereof, administered to a subject in a 24-hour period is any of the respective amounts described herein.

In embodiments, the pharmaceutical composition may be provided with conventional release or modified release profiles. The pharmaceutical composition may be provided at once or in multiple doses separated by an interval of time, e.g., 1 hour, 2 hours, 3 hours, 4 hours, 5 hours, 6 hours, 12 hours, etc. In other embodiments, multiple pharmaceutical compositions including (3S)-(+)-(5-chloro-2-methoxyphenyl)-1,3-dihydro-3-fluoro-6-(trifluoromethyl)-2H-indole-2-one or a pharmaceutically acceptable salt thereof, having different drug release profiles, may be provided to create a two-phase release profile. For example, a first pharmaceutical composition may be provided with an immediate release profile, e.g., ODDF, parenteral, etc., and a second pharmaceutical composition may provide an extended release profile. In embodiments, one or both of the first and second pharmaceutical compositions may be provided with an extended release or delayed release profile. Such compositions may be provided as pulsatile formulations, multi-layer tablets or capsules containing tablets, beads, granules, etc. In embodiments, the first pharmaceutical composition is an immediate release composition. In embodiments, the second pharmaceutical composition is an immediate release composition. In embodiments, the first and second pharmaceutical compositions are provided as separate immediate release compositions, e.g., film, tablets or capsules. In embodiments the first and second pharmaceutical compositions are provided 12 hours apart.

It should be understood that dosage amounts of (3S)-(+)-(5-chloro-2-methoxyphenyl)-1,3-dihydro-3-fluoro-6-(trifluoromethyl)-2H-indole-2-one or a pharmaceutically acceptable salt thereof, that are provided herein are applicable to all the dosage forms described herein including conventional dosage forms, modified dosage forms, any first and second pharmaceutical compositions with differing release profiles, as well as the parenteral formulations described herein. Those skilled in the art will determine appropriate amounts depending on criteria such as dosage form, route of administration, subject tolerance, efficacy, therapeutic goal and therapeutic benefit, among other pharmaceutically acceptable criteria.

Combination therapies utilizing more than one pharmaceutical composition possessing maxi-K channel openers, such as (3S)-(+)-(5-chloro-2-methoxyphenyl)-1,3-dihydro-3-fluoro-6-(trifluoromethyl)-2H-indole-2-one or a pharmaceutically acceptable salt thereof, or enantiomers thereof, the different pharmaceutical compositions having different release profiles, can include administration of the active agents together in the same admixture, or in separate admixtures.

In embodiments, the subject may be started at a low dose of the therapeutic agent and the dosage is escalated. In this manner, it can be determined if the drug is well tolerated in the subject. Dosages can be lower for children than for adults.

While the above disclosure has focused on embodiments utilizing (3S)-(+)-(5-chloro-2-methoxyphenyl)-1,3-dihydro-3-fluoro-6-(trifluoromethyl)-2H-indole-2-one, it is to be understood that the same dosage amounts, uses, methods, dosage forms, and the like described herein are equally applicable to any of the other maxi-K channel openers, such as the fluoro-oxindole and chloro-oxindole compounds described above, including (3R)-(−)-(5-chloro-2-methoxyphenyl)-1,3-dihydro-3-fluoro-6-(trifluoromethyl)-2H-indole-2-one, (3S)-(+)-(5-chloro-2-methoxyphenyl)-1,3-dihydro-3-chloro-6-(trifluoromethyl)-2H-indol-2-one, (3R)-(−)-(5-chloro-2-methoxyphenyl)-1,3-dihydro-3-chloro-6-(trifluoromethyl)-2H-indol-2-one, pharmaceutically acceptable salts of any of the foregoing, prodrugs of any of the foregoing, combinations thereof, and the like.

EXAMPLES

The examples provided herein are included solely for augmenting the disclosure herein and should not be considered to be limiting in any respect.

Example 1

Prospective Assessment of the Efficacy of (3S)-(+)-(5-chloro-2-methoxyphenyl)-1,3-dihydro-3-fluoro-6-(trifluoromethyl)-2H-indole-2-one in Pediatric Subjects with Status Epilepticus This study is designed to determine whether with (3S)-(+)-(5-chloro-2-methoxyphenyl)-1,3-dihydro-3-fluoro-6-(trifluoromethyl)-2H-indole-2-one leads to an improvement in one or more symptoms of status epilepticus. Epilepsy is among the most common serious neurologic disorders in childhood. Medicines with novel actions of mechanisms of action are needed to try to address the unmet clinical need for seizure control in subjects with status epilepticus. In addition, the purpose of this study is to evaluate the safety and tolerability of (3S)-(+)-(5-chloro-2-methoxyphenyl)-1,3-dihydro-3-fluoro-6-(trifluoromethyl)-2H-indole-2-one as treatment in subjects with status epilepticus.

(3S)-(+)-(5-chloro-2-methoxyphenyl)-1,3-dihydro-3-fluoro-6-(trifluoromethyl)-2H-indole-2-one or a pharmaceutically acceptable salt thereof will be administered intravenously to pediatric subjects (3 months to 16 years) in amounts ranging from 0.25, 0.5, 1, 1.5, 2, 2.5, 3, 4, 5, 6, 7, 8, 9, 10, 15, 25, 50 and 100 mg as 50 mL short-term infusion solution intravenously (IV) within 15 minutes (infusion rate 200 mL/h). Subjects whose seizure does not stop or recurs within 10 minutes after the initial dose may receive the same amount of (3S)-(+)-(5-chloro-2-methoxyphenyl)-1,3-dihydro-3-fluoro-6-(trifluoromethyl)-2H-indole-2-one injection no earlier than 10 minutes following the initial dose. Subjects whose seizure stops within 10 minutes after the initial dose, but recurs thereafter (within 12 hours) may receive the same amount of (3S)-(+)-(5-chloro-2-methoxyphenyl)-1,3-dihydro-3-fluoro-6-(trifluoromethyl)-2H-indole-2-one injection; a total of 2 doses will be permitted in this study.

Inclusion Criteria:
  Subjects with status epilepticus or repetitive status epilepticus/cluster seizure who have seizures that can be evaluated by investigator's visual observations based on motor symptoms or who have seizures that can be evaluated by EEG.
  Subjects with status epilepticus accompanied by generalized seizure, partial seizure or secondarily generalized seizure lasting 5 minutes or longer.
  Subjects with repetitive status epilepticus/cluster seizure accompanied by not less than 3 consecutive episodes of generalized seizure, partial seizure or secondarily generalized seizure in 1 hour.
  Subjects not younger than 3 months (either gender is eligible for the study).

Primary Outcome Measures:
  Percentage of Participants With Clinical Benefit. [Time Frame: 30 minutes]
  Percent of participants whose initial seizure stopped within 10 minutes after initial dose and who continued seizure-free for at least 30 minutes after the completion of initial dose (responder rate).

Secondary Outcome Measures:
  Percent of participants whose initial seizure stopped within 10 minutes after the administration of (3S)-(+)-(5-chloro-2-methoxyphenyl)-1,3-dihydro-3-fluoro-6-(trifluoromethyl)-2H-indole-2-one (either initial or second dose [in 10 to 30 minutes from the initial dose]) and who continued seizure-free for at least 30 minutes. [Time Frame: 1 hour]
  Percent of participants whose seizures stopped within 10 minutes after the administration of (3S)-(+)-(5-chloro-2-methoxyphenyl)-1,3-dihydro-3-fluoro-6-(trifluoromethyl)-2H-indole-2-one (only the initial dose) and who continued seizure-free for at least 12 hours post-dose. [Time Frame: 12 hours]
  Percent of participants whose seizures stopped within 10 minutes after the administration of (3S)-(+)-(5-chloro-2-methoxyphenyl)-1,3-dihydro-3-fluoro-6-(trifluoromethyl)-2H-indole-2-one (either initial or second dose [in 10 to 30 minutes from the initial dose]) and who continued seizure-free for at least 12 hours post-dose. [Time Frame: 12 hours]
  Percent of participants whose seizures stopped within 10 minutes after the administration of (3S)-(+)-(5-chloro-2-methoxyphenyl)-1,3-dihydro-3-fluoro-6-(trifluoromethyl)-2H-indole-2-one (only the initial dose) and who continued seizure-free for at least 24 hours post-dose. [Time Frame: 24 hours]
  Percent of participants whose seizures stopped within 10 minutes after the administration of (3S)-(+)-(5-chloro-2-methoxyphenyl)-1,3-dihydro-3-fluoro-6-(trifluoromethyl)-2H-indole-2-one (either initial or second dose [in 10 to 30 minutes from the initial dose]) and who continued seizure-free for at least 24 hours post-dose. [Time Frame: 24 hours]
  Time to resolution of seizures from the administration of (3S)-(+)-(5-chloro-2-methoxyphenyl)-1,3-dihydro-3-fluoro-6-(trifluoromethyl)-2H-indole-2-one (only the initial dose). [Time Frame: 24 hours]
  Time to resolution of seizures from the administration of (3S)-(+)-(5-chloro-2-methoxyphenyl)-1,3-dihydro-3-fluoro-6-(trifluoromethyl)-2H-indole-2-one (either initial or second dose). [Time Frame: 24 hours]
  Time to relapse from the resolution of seizures following the administration of (3S)-(+)-(5-chloro-2-methoxyphenyl)-1,3-dihydro-3-fluoro-6-(trifluoromethyl)-2H-indole-2-one (only the initial dose, within 24 hours). [Time Frame: 24 hours]
  Time to relapse from the resolution of seizures following the administration of (3S)-(+)-(5-chloro-2-methoxyphenyl)-1,3-dihydro-3-fluoro-6-(trifluoromethyl)-2H-indole-2-one (either initial or second dose, within 24 hours). [Time Frame: 24 hours]

Example 2

Prospective Assessment of the Efficacy of (3S)-(+)-(5-chloro-2-methoxyphenyl)-1,3-dihydro-3-fluoro-6-(trifluoromethyl)-2H-indole-2-one in Adult Subjects with Status Epilepticus This study is designed to determine whether with (3S)-(+)-(5-chloro-2-methoxyphenyl)-1,3-dihydro-3-fluoro-6-(trifluoromethyl)-2H-indole-2-one leads to an improvement in one or more symptoms of status epilepticus in adults. In addition, the purpose of this study is to evaluate the safety and tolerability of (3S)-(+)-(5-chloro-2-methoxyphenyl)-1,3-dihydro-3-fluoro-6-(trifluoromethyl)-2H-indole-2-one as treatment in subjects with status epilepticus.

(3S)-(+)-(5-chloro-2-methoxyphenyl)-1,3-dihydro-3-fluoro-6-(trifluoromethyl)-2H-indole-2-one or a pharmaceutically acceptable salt thereof will be administered intravenously to adult subjects (older than 16 years) in amounts ranging from 0.1, 0.2, 0.4, 0.6, 0.8, 1, 1.2, 1.4, 1.6, 1.8, and 2 mg/kg as 50 mL short-term infusion solution intravenously (IV) within 15 minutes (infusion rate 200 mL/h). Subjects whose seizure does not stop or recurs within 10 minutes after the initial dose may receive the same amount of (3S)-(+)-(5-chloro-2-methoxyphenyl)-1,3-dihydro-3-fluoro-6-(trifluoromethyl)-2H-indole-2-one injection no earlier than 10 minutes following the initial dose. Subjects whose seizure stops within 10 minutes after the initial dose, but recurs thereafter (within 12 hours) may receive the same amount of (3S)-(+)-(5-chloro-2-methoxyphenyl)-1,3-dihydro-3-fluoro-6-(trifluoromethyl)-2H-indole-2-one injection; a total of 2 doses will be permitted in this study.

Inclusion Criteria:
  Subjects with status epilepticus or repetitive status epilepticus/cluster seizure who have seizures that can be evaluated by investigator's visual observations based on motor symptoms or who have seizures that can be evaluated by EEG.
  Subjects with status epilepticus accompanied by generalized seizure, partial seizure or secondarily generalized seizure lasting 5 minutes or longer.
  Subjects with repetitive status epilepticus/cluster seizure accompanied by not less than 3 consecutive episodes of generalized seizure, partial seizure or secondarily generalized seizure in 1 hour.
  Either gender is eligible for the study.

Primary Outcome Measures:
Percentage of Participants With Clinical Benefit. [Time Frame: 30 minutes]
Percent of participants whose initial seizure stopped within 10 minutes after initial dose and who continued seizure-free for at least 30 minutes after the completion of initial dose (responder rate).
Secondary Outcome Measures:
Percent of participants whose initial seizure stopped within 10 minutes after the administration of (3S)-(+)-(5-chloro-2-methoxyphenyl)-1,3-dihydro-3-fluoro-6-(trifluoromethyl)-2H-indole-2-one (either initial or second dose [in 10 to 30 minutes from the initial dose]) and who continued seizure-free for at least 30 minutes. [Time Frame: 1 hour]
Percent of participants whose seizures stopped within 10 minutes after the administration of (3S)-(+)-(5-chloro-2-methoxyphenyl)-1,3-dihydro-3-fluoro-6-(trifluoromethyl)-2H-indole-2-one (only the initial dose) and who continued seizure-free for at least 12 hours post-dose. [Time Frame: 12 hours]
Percent of participants whose seizures stopped within 10 minutes after the administration of (3S)-(+)-(5-chloro-2-methoxyphenyl)-1,3-dihydro-3-fluoro-6-(trifluoromethyl)-2H-indole-2-one (either initial or second dose [in 10 to 30 minutes from the initial dose]) and who continued seizure-free for at least 12 hours post-dose. [Time Frame: 12 hours]
Percent of participants whose seizures stopped within 10 minutes after the administration of (3S)-(+)-(5-chloro-2-methoxyphenyl)-1,3-dihydro-3-fluoro-6-(trifluoromethyl)-2H-indole-2-one (only the initial dose) and who continued seizure-free for at least 24 hours post-dose. [Time Frame: 24 hours]
Percent of participants whose seizures stopped within 10 minutes after the administration of (3S)-(+)-(5-chloro-2-methoxyphenyl)-1,3-dihydro-3-fluoro-6-(trifluoromethyl)-2H-indole-2-one (either initial or second dose [in 10 to 30 minutes from the initial dose]) and who continued seizure-free for at least 24 hours post-dose. [Time Frame: 24 hours]
Time to resolution of seizures from the administration of (3S)-(+)-(5-chloro-2-methoxyphenyl)-1,3-dihydro-3-fluoro-6-(trifluoromethyl)-2H-indole-2-one (only the initial dose). [Time Frame: 24 hours]
Time to resolution of seizures from the administration of (3S)-(+)-(5-chloro-2-methoxyphenyl)-1,3-dihydro-3-fluoro-6-(trifluoromethyl)-2H-indole-2-one (either initial or second dose). [Time Frame: 24 hours]
Time to relapse from the resolution of seizures following the administration of (3S)-(+)-(5-chloro-2-methoxyphenyl)-1,3-dihydro-3-fluoro-6-(trifluoromethyl)-2H-indole-2-one (only the initial dose, within 24 hours). [Time Frame: 24 hours]
Time to relapse from the resolution of seizures following the administration of (3S)-(+)-(5-chloro-2-methoxyphenyl)-1,3-dihydro-3-fluoro-6-(trifluoromethyl)-2H-indole-2-one (either initial or second dose, within 24 hours). [Time Frame: 24 hours]

It should be understood that the examples and embodiments provided herein are exemplary examples embodiments. Those skilled in the art will envision various modifications of the examples and embodiments that are consistent with the scope of the disclosure herein. Such modifications are intended to be encompassed by the claims.

What is claimed is:

1. A method of treating CDKL5 disorder comprising administering to a subject with the CDKL5 disorder a maxi-K channel opener or a pharmaceutically acceptable salt thereof in an amount of from 0.05 mg to 1500 mg.

2. The method of treating a CDKL5 disorder according to claim 1, wherein the maxi-K channel opener is selected from the group consisting of fluoro-oxindole and chloro-oxindole compounds.

3. The method of treating a CDKL5 disorder according to claim 2, wherein the fluoro-oxindole is selected from the group consisting of (3S)-(+)-(5-chloro-2-methoxyphenyl)-1,3-dihydro-3-fluoro-6-(trifluoromethyl)-2H-indole-2-one or a pharmaceutically acceptable salt thereof, (3R)-(−)-(5-chloro-2-methoxyphenyl)-1,3-dihydro-3-fluoro-6-(trifluoromethyl)-2H-indole-2-one or a pharmaceutically acceptable salt thereof, and combinations thereof.

4. The method of treating a CDKL5 disorder according to claim 2, wherein the chloro-oxindole is selected from the group consisting of (3S)-(+)-(5-chloro-2-methoxyphenyl)-1,3-dihydro-3-chloro-6-(trifluoromethyl)-2H-indol-2-one or a pharmaceutically acceptable salt thereof, (3R)-(−)-(5-chloro-2-methoxyphenyl)-1,3-dihydro-3-chloro-6-(trifluoromethyl)-2H-indol-2-one or a pharmaceutically acceptable salt thereof, and combinations thereof.

5. The method of treating a CDKL5 disorder according to claim 3, wherein the subject is administered from 0.1 mg to 200 mg of (3S)-(+)-(5-chloro-2-methoxyphenyl)-1,3-dihydro-3-fluoro-6-(trifluoromethyl)-2H-indole-2-one or a pharmaceutically acceptable salt thereof.

6. The method of treating a CDKL5 disorder according to claim 3, wherein the subject is administered from 5 mg to 150 mg of (3S)-(+)-(5-chloro-2-methoxyphenyl)-1,3-dihydro-3-fluoro-6-(trifluoromethyl)-2H-indole-2-one or a pharmaceutically acceptable salt thereof.

7. The method of treating a CDKL5 disorder according to claim 3, wherein the total amount of (3S)-(+)-(5-chloro-2-methoxyphenyl)-1,3-dihydro-3-fluoro-6-(trifluoromethyl)-2H-indole-2-one, or a pharmaceutically acceptable salt thereof, administered to the subject in a twenty-four hour period is between 0.05 mg and 600 mg.

8. The method of treating a CDKL5 disorder according to claim 3, wherein (3S)-(+)-(5-chloro-2-methoxyphenyl)-1,3-dihydro-3-fluoro-6-(trifluoromethyl)-2H-indole-2-one or pharmaceutically acceptable salt thereof is administered to the subject from one to four times a day.

9. The method of treating a CDKL5 disorder according to claim 1, wherein administering is accomplished via a route selected from the group consisting of oral, buccal, sublingual, rectal, topical, intranasal, vaginal and parenteral.

10. The method of treating a CDKL5 disorder according to claim 1, wherein the method provides improvement in at least one symptom selected from the group consisting of ataxia, gait impairment, speech impairment, vocalization, impaired cognition, abnormal motor activity, clinical seizure, subclinical seizure, hypotonia, hypertonia, drooling, mouthing behavior, aura, convulsions, repetitive movements, unusual sensations, frequency of seizures and severity of seizures.

11. A method of treating a CDKL5 disorder comprising administering to a subject with the CDKL5 (3S)-(+)-(5-chloro-2-methoxyphenyl)-1,3-dihydro-3-fluoro-6-(trifluoromethyl)-2H-indole-2-one or a pharmaceutically acceptable salt thereof, in an amount of from 0.05 mg to 1500 mg.

12. The method of treating a CDKL5 disorder according to claim 11, wherein the subject is administered from 0.1 mg to 200 mg of (3S)-(+)-(5-chloro-2-methoxyphenyl)-1,3-di hydro-3-fluoro-6-(trifluoromethyl)-2H-indole-2-one or a pharmaceutically acceptable salt thereof.

13. The method of treating a CDKL5 disorder according to claim 11, wherein the subject is administered from 5 mg to 150 mg of (3S)-(+)-(5-chloro-2-methoxyphenyl)-1,3-dihydro-3-fluoro-6-(trifluoromethyl)-2H-indole-2-one or a pharmaceutically acceptable salt thereof.

14. The method of treating a CDKL5 disorder according to claim 11, wherein the total amount of (3S)-(+)-(5-chloro-2-methoxyphenyl)-1,3-dihydro-3-fluoro-6-(trifluoromethyl)-2H-indole-2-one or a pharmaceutically acceptable salt thereof administered to the subject in a twenty-four hour period is between 0.05 mg and 600 mg.

15. The method of treating a CDKL5 disorder according to claim 11, wherein (3S)-(+)-(5-chloro-2-methoxyphenyl)-1,3-dihydro-3-fluoro6-(trifluoromethyl)-2H-indole-2-one or a pharmaceutically acceptable salt thereof is administered from one to four times a day.

16. The method of treating a CDKL5 disorder according to claim 11, wherein administering is accomplished via a route selected from the group consisting of oral, buccal, sublingual, rectal, topical, intranasal, vaginal and parenteral.

17. The method of treating a CDKL5 disorder according to claim 11, wherein the method provides improvement in at least one symptom selected from the group consisting of ataxia, gait impairment, speech impairment, vocalization, impaired cognition, abnormal motor activity, clinical seizure, subclinical seizure, hypotonia, hypertonia, drooling, mouthing behavior, aura, convulsions, repetitive movements, unusual sensations, frequency of seizures and severity of seizures.

\* \* \* \* \*